(12) United States Patent
Bruce

(10) Patent No.: US 8,939,032 B2
(45) Date of Patent: Jan. 27, 2015

(54) MOBILE ANCHOR TESTER

(71) Applicant: Wallace Bruce, Pampa, TX (US)

(72) Inventor: Wallace Bruce, Pampa, TX (US)

(*) Notice: Subject to any disclaimer, the term of this patent is extended or adjusted under 35 U.S.C. 154(b) by 270 days.

(21) Appl. No.: 13/656,870

(22) Filed: Oct. 22, 2012

(65) Prior Publication Data

US 2013/0098165 A1  Apr. 25, 2013

Related U.S. Application Data

(60) Provisional application No. 61/550,100, filed on Oct. 21, 2011, provisional application No. 61/558,710, filed on Nov. 11, 2011, provisional application No. 61/559,965, filed on Nov. 15, 2011.

(51) Int. Cl.
*G01N 3/08* (2006.01)
*G01M 5/00* (2006.01)

(52) U.S. Cl.
CPC *G01N 3/08* (2013.01); *G01M 5/005* (2013.01)
USPC .................................. 73/826; 73/784

(58) Field of Classification Search
CPC ..... G01L 5/0033; G01M 17/007; G01N 3/10; E02D 33/00
USPC .................... 73/760, 784, 828, 826
See application file for complete search history.

(56) References Cited

U.S. PATENT DOCUMENTS

| | | | |
|---|---|---|---|
| 3,571,956 A * | 3/1971 | Heiberg | 37/367 |
| 3,583,514 A * | 6/1971 | Taylor | 180/401 |
| 3,666,123 A * | 5/1972 | Tornheim | 414/557 |
| 3,673,970 A * | 7/1972 | Hatcher | 111/186 |
| 3,738,163 A | 6/1973 | McEntire | |
| 4,657,087 A * | 4/1987 | Livneh | 172/3 |
| 5,216,922 A * | 6/1993 | Gustafson et al. | 73/784 |
| 5,404,757 A * | 4/1995 | Soulard | 73/784 |
| 5,679,904 A | 10/1997 | Stets et al. | |
| 5,792,961 A | 8/1998 | Giebner et al. | |
| 5,798,467 A | 8/1998 | Hasegawa et al. | |
| 5,810,097 A * | 9/1998 | McMillan | 172/782 |
| 5,876,174 A * | 3/1999 | Arsenault | 414/460 |
| 5,880,374 A * | 3/1999 | MacKarvich | 73/804 |
| 6,014,901 A | 1/2000 | Boe | |
| 6,041,660 A | 3/2000 | Fujitaka et al. | |
| 6,240,788 B1 | 6/2001 | Balestracci | |
| 6,648,078 B1 * | 11/2003 | Moffett et al. | 172/788 |
| 8,220,339 B1 * | 7/2012 | Scherbring | 73/784 |
| 2008/0184808 A1 | 8/2008 | Berra | |

* cited by examiner

*Primary Examiner* — Max Noori
(74) *Attorney, Agent, or Firm* — Jackson Walker, LLP

(57) ABSTRACT

A mobile anchor tester for testing an earth anchor or a deadman or any other suitable assembly. A mobile system is provided for testing in-ground anchors, the system including a mobile platform, such as a trailer or the bed of a pickup truck having a horizontal support surface spaced above the ground. A pair of adjustable leg assemblies are provided engaging the rear end of the mobile anchor tester. The legs are adjustable, typically having hydraulic cylinders engaged therewith. The adjustable leg assemblies will extend from the back or rear end of the mobile platform to the ground. An anchor testing assembly engaged with the horizontal support surface on the mobile platform has a cable at the removed end thereof. The cable includes a hook to engage the in-ground anchor.

21 Claims, 19 Drawing Sheets

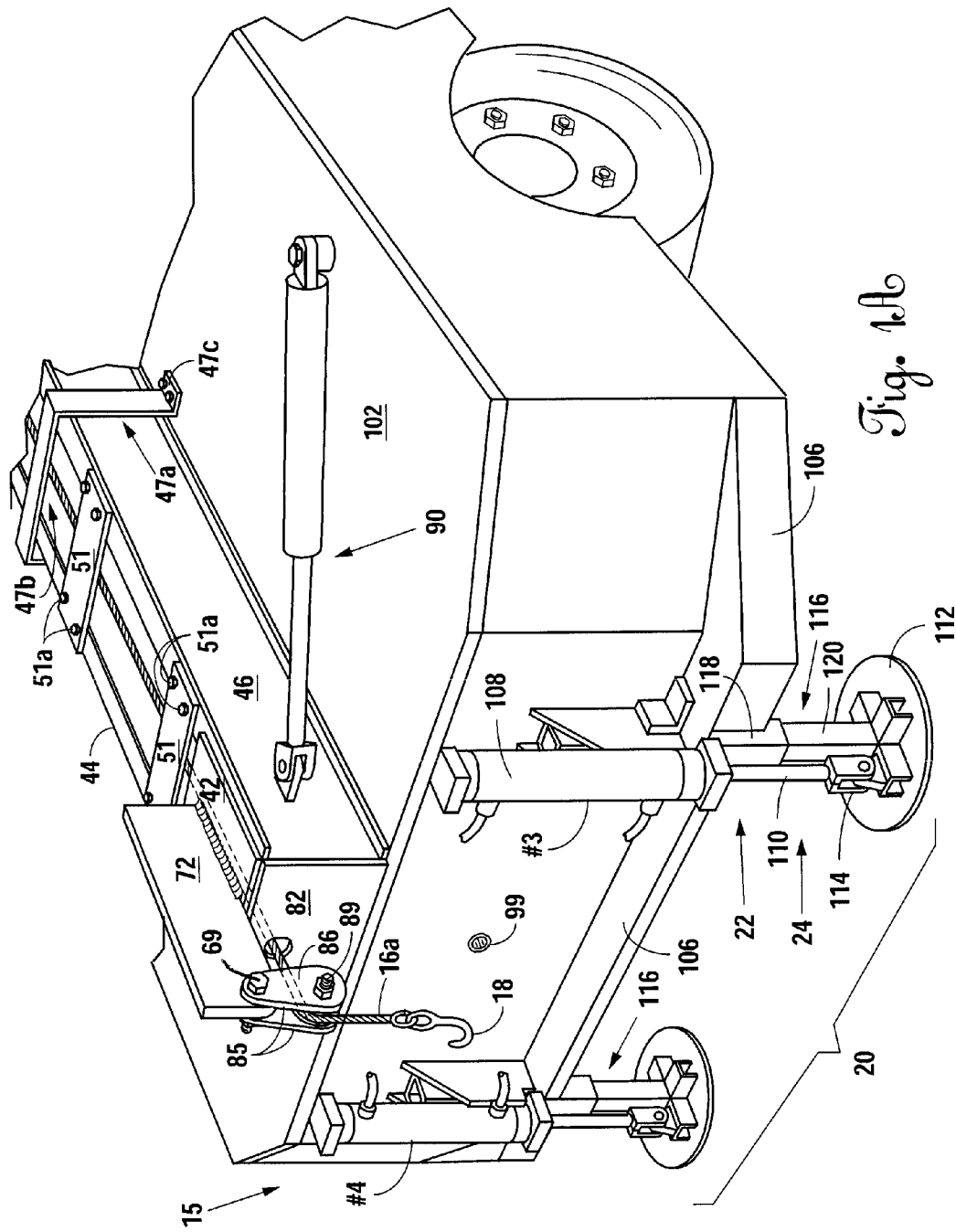

US 8,939,032 B2

MOBILE ANCHOR TESTER

This application claims benefit of and incorporates herein by reference, U.S. Provisional Patent Application Nos. 61/550,100, filed Oct. 21, 2011; 61/558,710, filed Nov. 11, 2011; and 61/559,965, filed Nov. 15, 2011.

FIELD OF THE INVENTION

Anchor testers, more specifically, a mobile anchor tester for testing an earth anchor or deadman or any suitable component.

BACKGROUND OF THE INVENTION

Earth anchors or deadmen are designed to attach something, for example, a tower via a cable, to the earth. They are designed to withstand tension. Anchor testers are devices that will apply tension to the removed end (the end exposed from the earth) of an earth anchor or deadman. Anchors may be tested to a maximum pressure and held there for a period of time, and then pressure is released.

SUMMARY OF THE INVENTION

Applicant discloses a mobile system for testing in-ground anchors or other components, the system comprising a mobile platform, such as a trailer, having a horizontal support surface spaced above the ground, a front, and a rear; an anchor testing assembly engaging the horizontal support surface, having a cable at a removed end adapted to engage the in-ground anchor and applying a tensile force thereto; a first adjustable leg assembly engaged with the mobile platform extendable and retractable therefrom, the removed end thereof capable of reaching the ground when in an extended position; and a second adjustable leg assembly engaged with the mobile platform extendable and retractable therefrom, the removed end thereof capable of reaching the ground.

In certain embodiments, the mobile platform is a truck or a trailer, the anchor testing assembly includes a first cylinder, such as a double acting hydraulic cylinder or other suitable means, adapted to apply tension to the cable; and the first and second adjustable legs comprise second and third double acting hydraulic cylinders or other suitable extensible means.

Particular embodiments further include means to selectively apply hydraulic force to the double acting hydraulic cylinders, and the anchor testing assembly includes a frame configured to receive the double acting cylinder, the frame lay adjacent the horizontal support surface of the mobile platform, the frame pivotally attached at a near end thereof to the horizontal support surface of the mobile platform, with the removed end of the double acting cylinder engaging the cable.

In some embodiments, the frame comprises longitudinal members adapted to secure the near end of the first cylinder thereto, wherein the first cylinder comprises a barrel and a rod, and wherein the cable is attached to the removed end of the rod, wherein the frame further includes a pulley for engaging the removed end thereof, the pulley for entraining thereon, the cable, wherein the frame is engaged with a fourth double acting cylinder, the fourth double acting cylinder for further engaging the horizontal support surface and the frame such that the removed end of the frame moves in an arc, the arc in a plane parallel to the horizontal support surface.

In one embodiment, the fluid circuit designed to selectively apply hydraulic pressure to the first cylinder includes means to record the magnitude of the application of pressure to the first double acting cylinder as a function of time.

Applicants also disclose a method for testing a component, such as a ground anchor. A ground anchor having an embedded portion and longitudinal member attached to the embedded portion and extending outward from the ground, the longitudinal member having a removed end is tested with a method comprising the steps of positioning the mobile platform such that a pulley is substantially aligned with an imaginary axis extending beyond the removed end of the longitudinal axis; attaching the removed end of the cable to the removed end of the longitudinal member; and applying hydraulic pressure to a first hydraulic cylinder so a to create tension in the longitudinal member. The tension is recorded over the period of time it is applied.

BRIEF DESCRIPTION OF THE DRAWINGS

FIG. 1A is a rear perspective view of the mobile anchor tester showing the frame and the first and second adjustable leg assemblies and other elements of Applicant's system for testing in-ground anchors.

FIG. 3A is a cross-sectional view showing an anti-lift brace.

FIG. 4A is a detailed front elevational view of the pulley assembly located at the removed end of the frame of the tension application assembly.

DETAILED DESCRIPTION OF THE PREFERRED EMBODIMENT

FIGS. 1-8 illustrate various implementations of Applicant's mobile anchor tester. Applicant's mobile anchor tester is designed to be transportable in the field to the site of the anchor to be tested, which anchor is typically in situ. That is to say, Applicant's mobile anchor tester 12 is typically moved to the location where the anchor is imbedded in the ground, with an arm AN extending therefrom, for example, see FIG. 1.

In one embodiment, Applicant provides a wheel and axle bearing mobile support platform 12 in the form of a truck. In another embodiment, Applicant provides a mobile support platform 12a having wheels and axle(s) in the form of a trailer, which trailer may be engaged to a truck, such as a pickup truck or other suitable vehicle. Mobile support platforms 12/12a may include rear ends 15/15a and horizontal support surface, such as a support plate 102 thereon (see FIG. 3).

Figure 10:
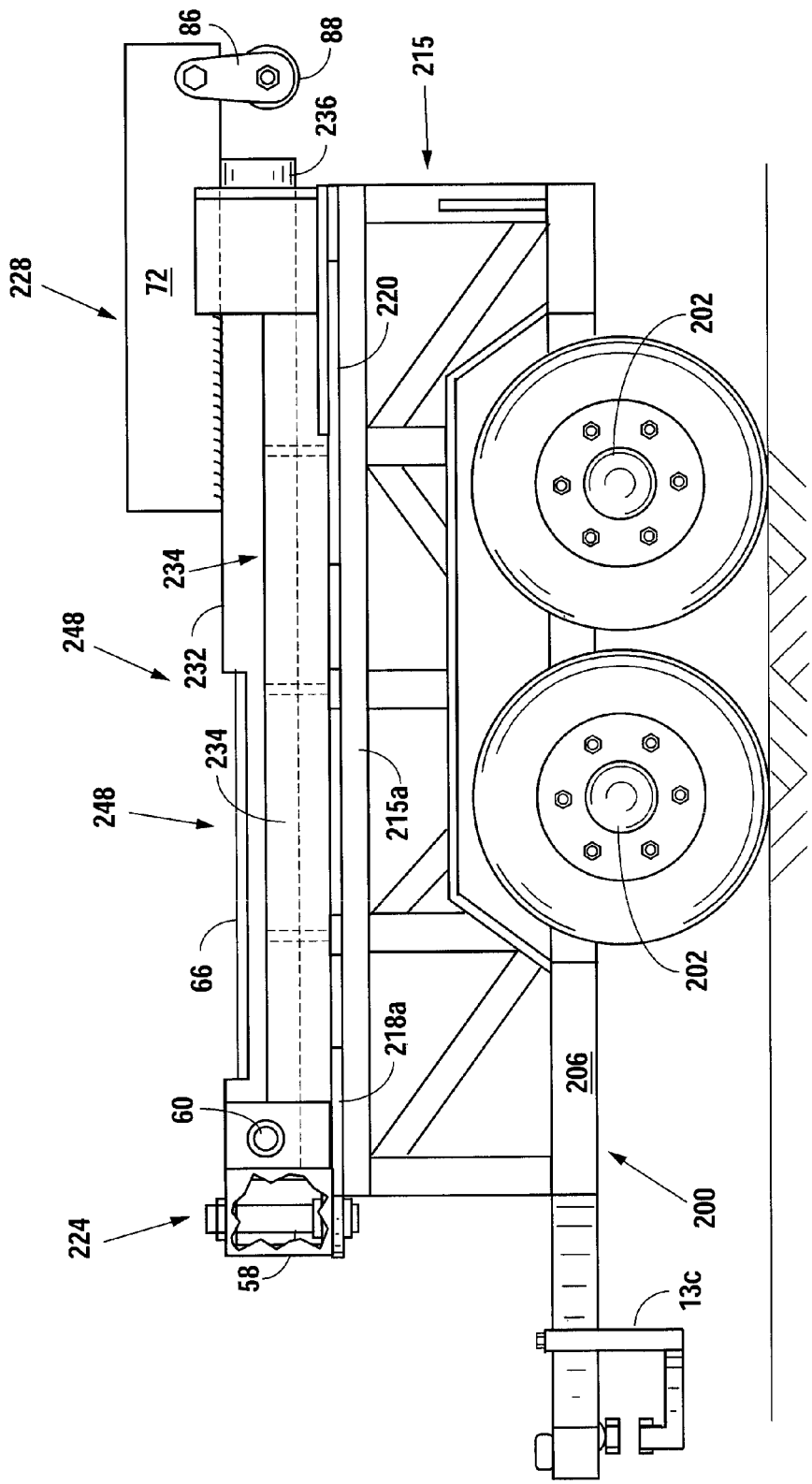
FIG. 10 is a side elevational view of some of the elements of Applicant's second trailer-based implementation.
Figure 11:
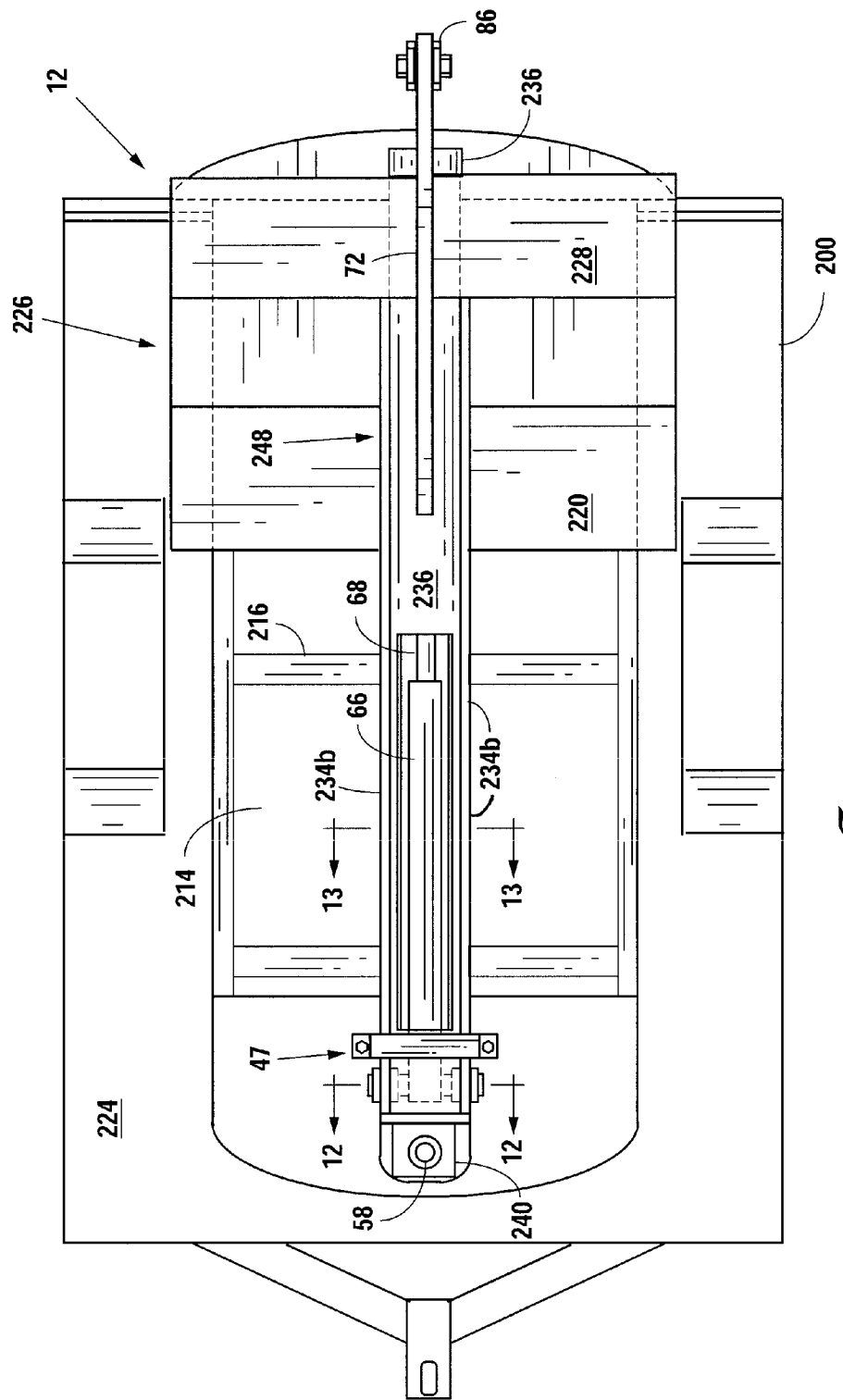
FIG. 11 is a top elevational view of the second trailer-based implementation with some elements omitted for clarity, but illustrating other details of the anchor engagement unit.
Figure 12:
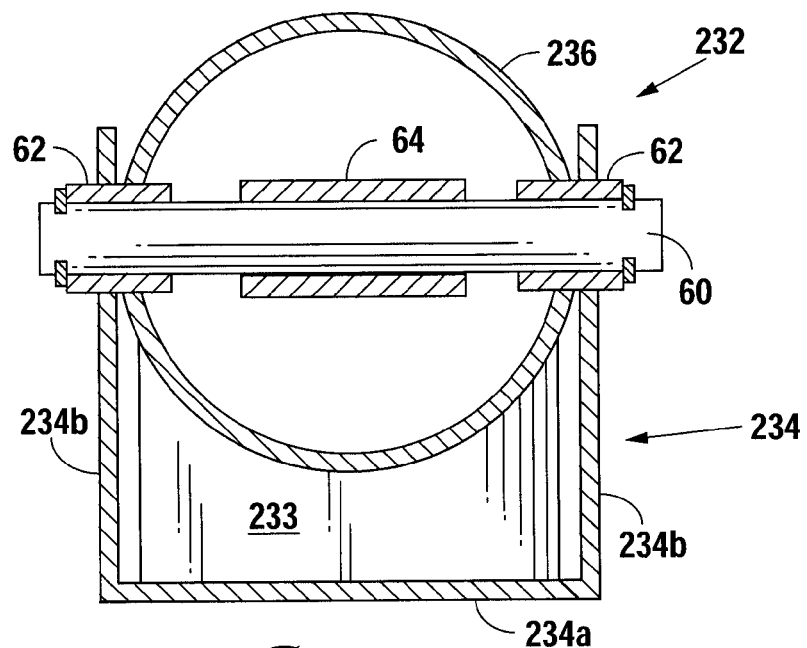
FIGS. 12 and 13 are cross-sectional views of the sections illustrated in FIG. 11, showing the nature of the structure illustrated to rigidly maintain the integrity of the frame assembly while the anchor is being tested.

An anchor testing assembly, including an engagement unit 14 is provided, which typically includes a cable 16 with a hook 18 engaged with a removed end 16a thereof. Near end 16b of cable 16 is engaged with cylinder No. 1 (see FIGS. 2 and 4). Cylinder No. 1 may include a barrel 66 with an arm 68 extending therefrom. A rear end of barrel 66 is pivotally coupled to an axle 60 and support plate 102 as seen in FIGS. 3 and 10. In certain modes, cylinder No. 1 and possibly cylinders Nos. 1-4, are double acting hydraulic cylinders. Arm 68 may extend and retract from barrel 66 (responsive to operation input) to move the hook 18, which typically is engaged to an eye or other removed end of arm AN. Cylinder No. 1 is designed therefor to apply and release tension through cable 16 to arm AN through action of cylinder No. 1, which may, for example, operate by hydraulic techniques.

Figure 1:
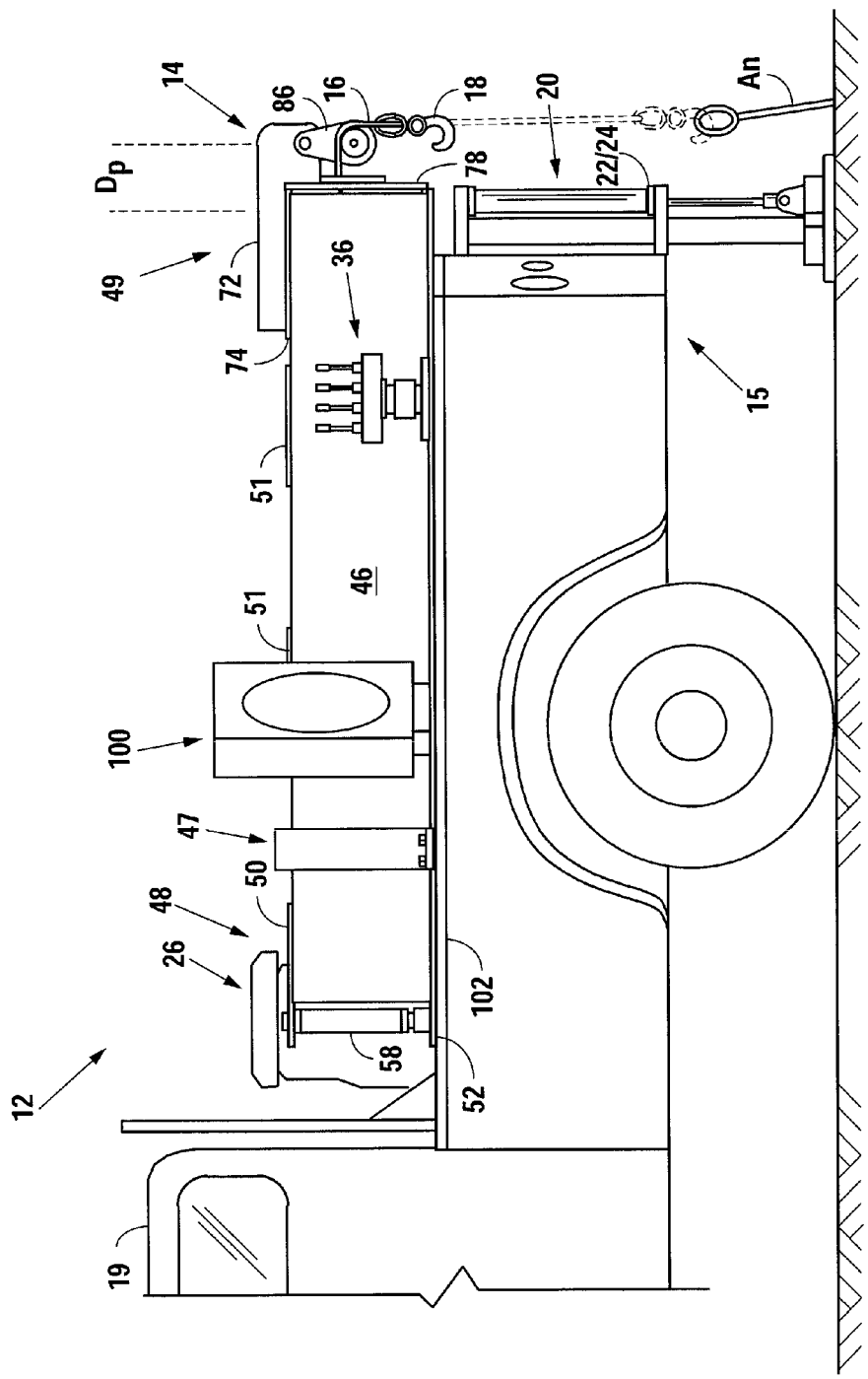
FIG. 1 is a side elevational view of an example implementation of Applicant's mobile anchor tester. Ghosted lines show cable extended and hooked to arm AN.

Applicant's mobile support platforms 12/12a further include an adjustable support leg assembly 20, which may include a first leg assembly 22 and a second leg assembly 24. Leg assemblies 22 and 24 are spaced about and engaged to rear end 15 and extend generally vertically downward as seen, for example, in FIGS. 1 and 1A, or slightly outward with relation to horizontal support surface as seen, for example, in FIG. 1B. The function of the adjustable support leg assembly 20 is to engage the rear end of the mobile support platforms 12/12a to the earth and to resist compression when tension is applied to cable 16. Furthermore, since each of assemblies 22/24 is adjustable in length and with feet 112, it will be seen that, if horizontal support surface is on an incline or tilted, it may be leveled somewhat through the use of independently adjustable support leg assembly 20 as more specifically set forth below. FIG. 1A also illustrates video camera 99 typically mounted approximately beneath the pulley and centered on the pulley, mounted to rear end 15 so as to allow the driver of the truck or other mobile platform to align with the anchor. A visual display (not shown) may be provided in cab 19, for viewing by the driver of the camera image.

It is seen that a frame 42 is provided as part of unit 14 for engaging cylinder No. 1. Cylinder No. 1 is adapted to apply tension in cable 16 when cable 16 is engaged to arm AN. Moreover, frame 42 is seen to be pivotable (fixed in an embodiment not shown) in an arc, that is, pivotable when seen in the top view set forth with respect to FIGS. 6, 7, and 8, about pivot pin 58. Frame 42 is anchored to support plate 102 (which in turn is rigidly mounted to mobile support platform 12) at near end 48. Removed end 49 may move in an arc and will help position hook 18 at the anchor arm AN as seen in FIG. 1 (ghosted).

Figure 6:
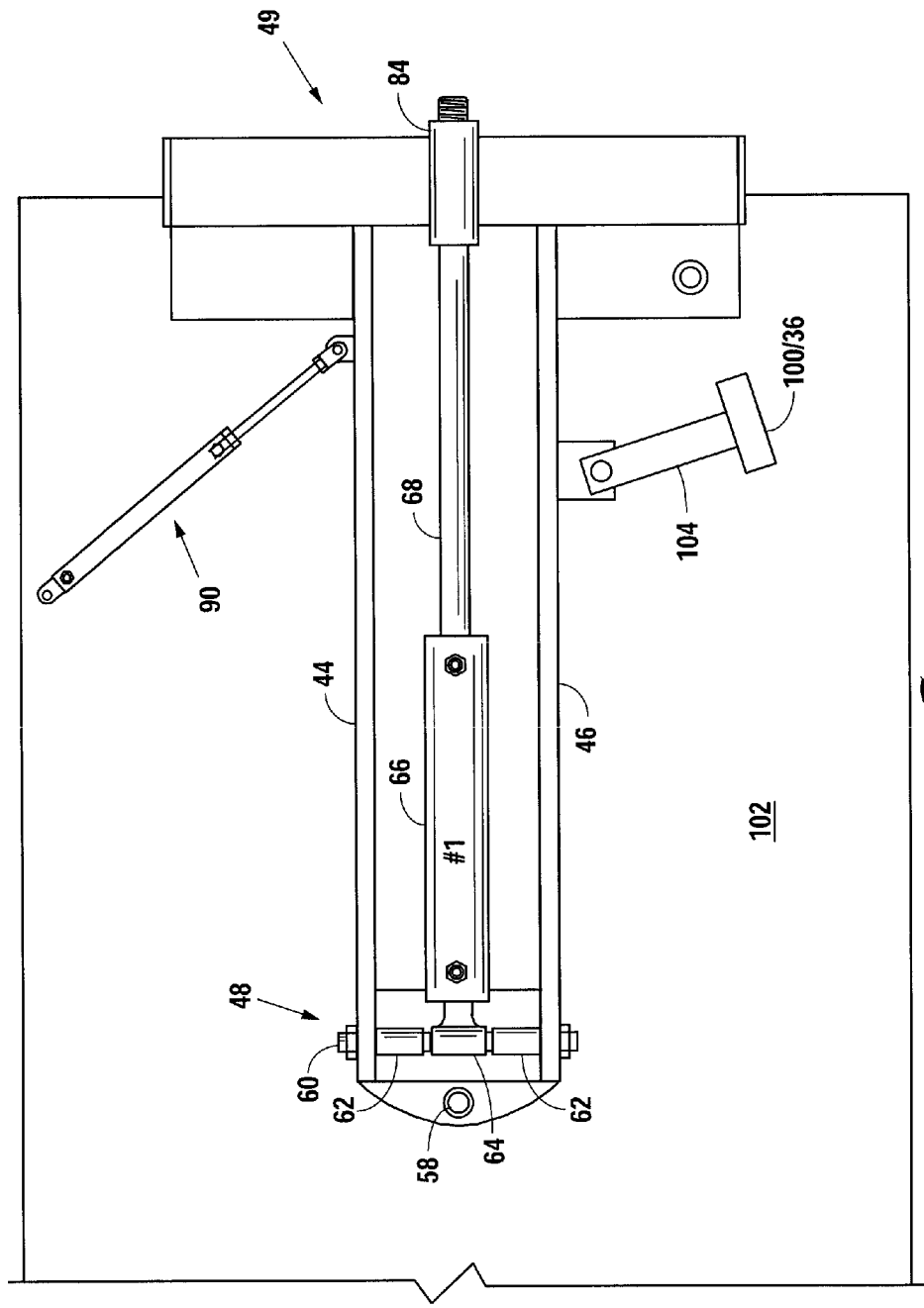
FIGS. 6, 7, and 8 are top elevational views of the frame of the tension application assembly with a lateral adjusting assembly in various positions with respect to a longitudinal axis of the mobile platform.
Figure 7:
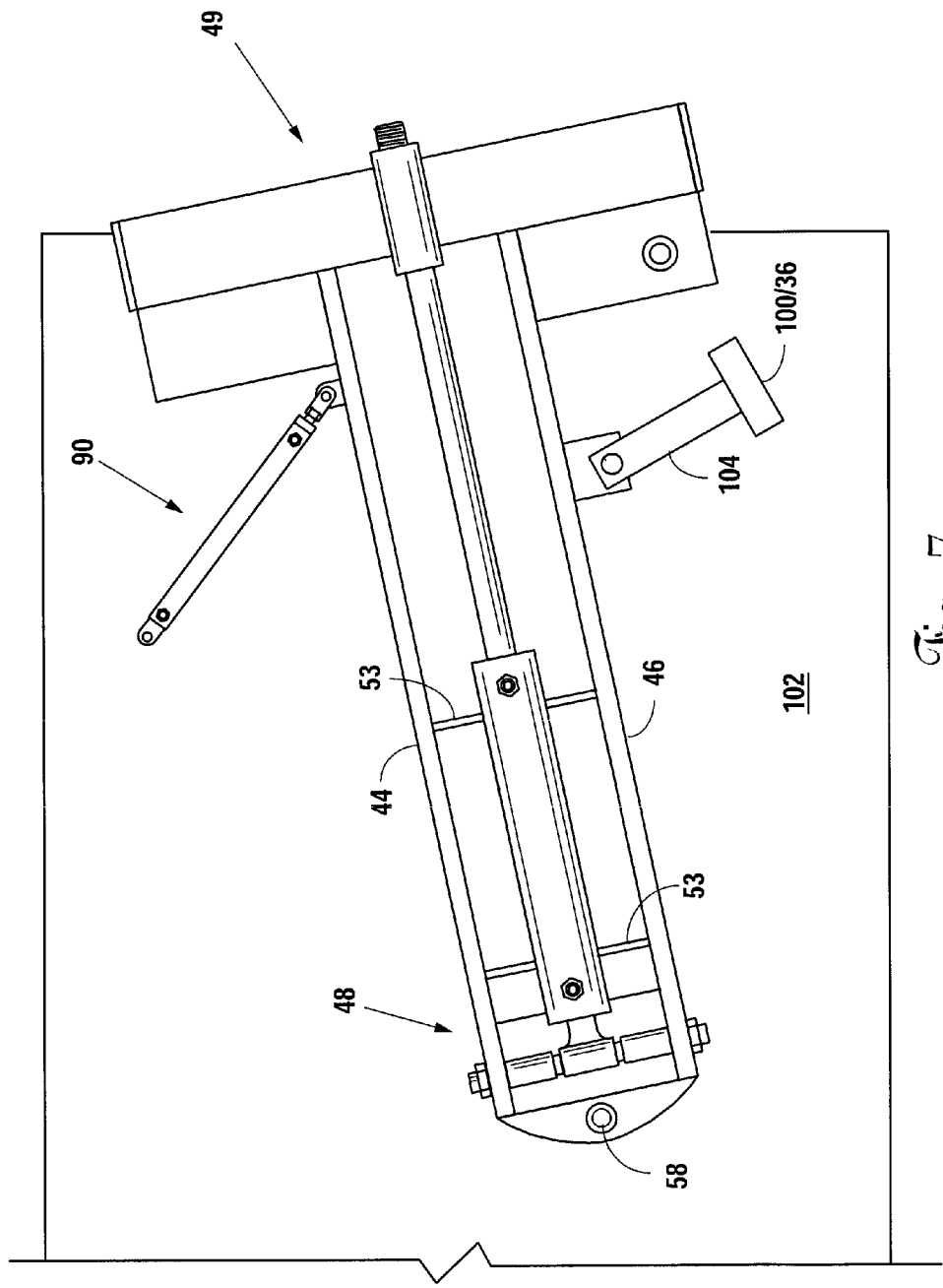
Figure 8:
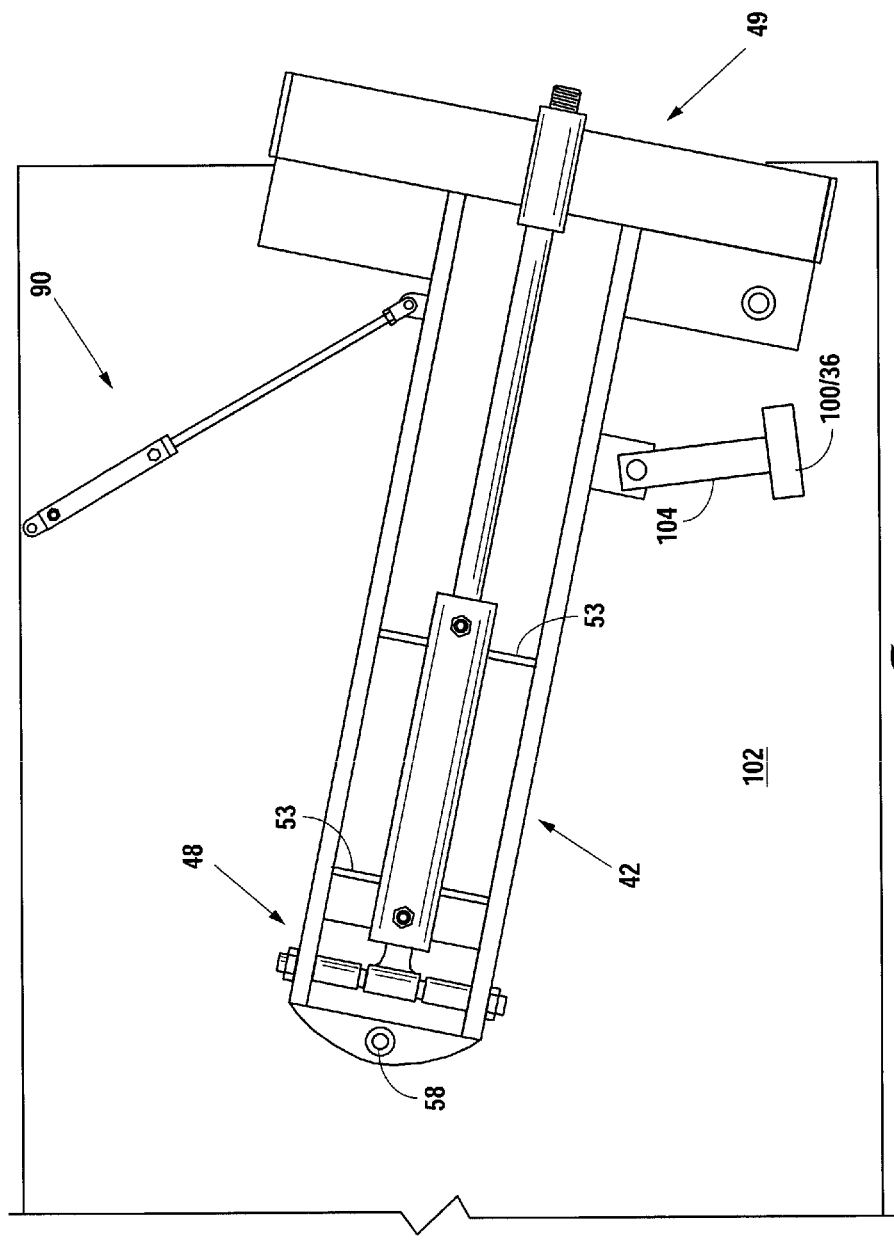

Frame 42 may have a pair of spaced apart side members 44 and 46, which side members are spaced about cylinder No. 1 as seen, for example, in FIG. 6. Side members 44/46 may be steel I-beams or other suitable member. Turning now to near end 48, it is seen to include a top plate 50 and a bottom plate 52, the top plate and bottom plate having bushings 54/56. Top and bottom plates 50/52 are coupled (e.g., welded) to the near end top surfaces of the two side plates and the bottom surface of the two plates, respectively, for rigidity and to resist twisting forces. Both plates typically are cut out at the bushings to receive pivot pin 58, which pivot pin is rigidly mounted perpendicular to horizontal support plate 102. Near end 48 also includes bushings 62 to maintain an axle 60, which will engage a sleeve or collar 64 at a near end of barrel 66 of cylinder No. 1, so as to allow some sliding or pivoting of the barrel slightly, although not a lot of such movement occurs.

Turning to removed end 49 of frame 42, a pulley mounting plate 72 is provided perpendicular to a top plate 74. Top plate 74 is coupled (e.g., welded) to the top removed end of the two side members 44/46. Likewise, the bottom plate 76 is coupled to the removed end of the bottom side of the two side members. An end plate 78 will help box structure generated by plates 74/76. Further, Applicants provide two cross-plates, front 80, rear 82, to which a tube 84 is provided generally aligned with and for receiving cable 16 therethrough, so as to maintain cable 16 aligned with pulley bracket 86 and pulley 88 therein. In certain implementations, tube 84 may be approximately 5 inches long and ½ inch in diameter.

Figure 2:
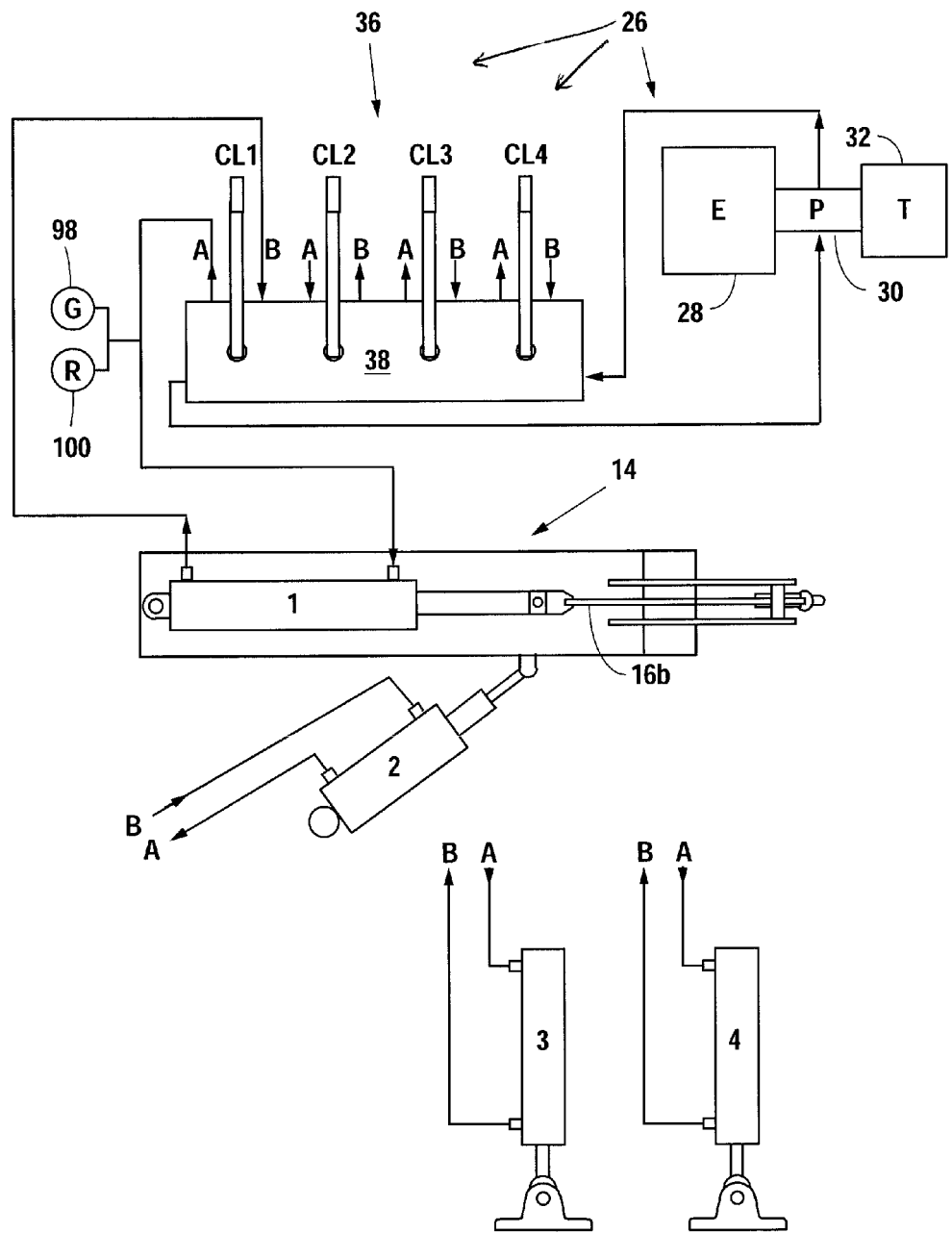
FIG. 2 is a combined schematic/equipment illustration of the hydraulic distribution system and related line connecting the four hydraulic cylinders of Applicant's mobile anchor tester.
Figure 3:
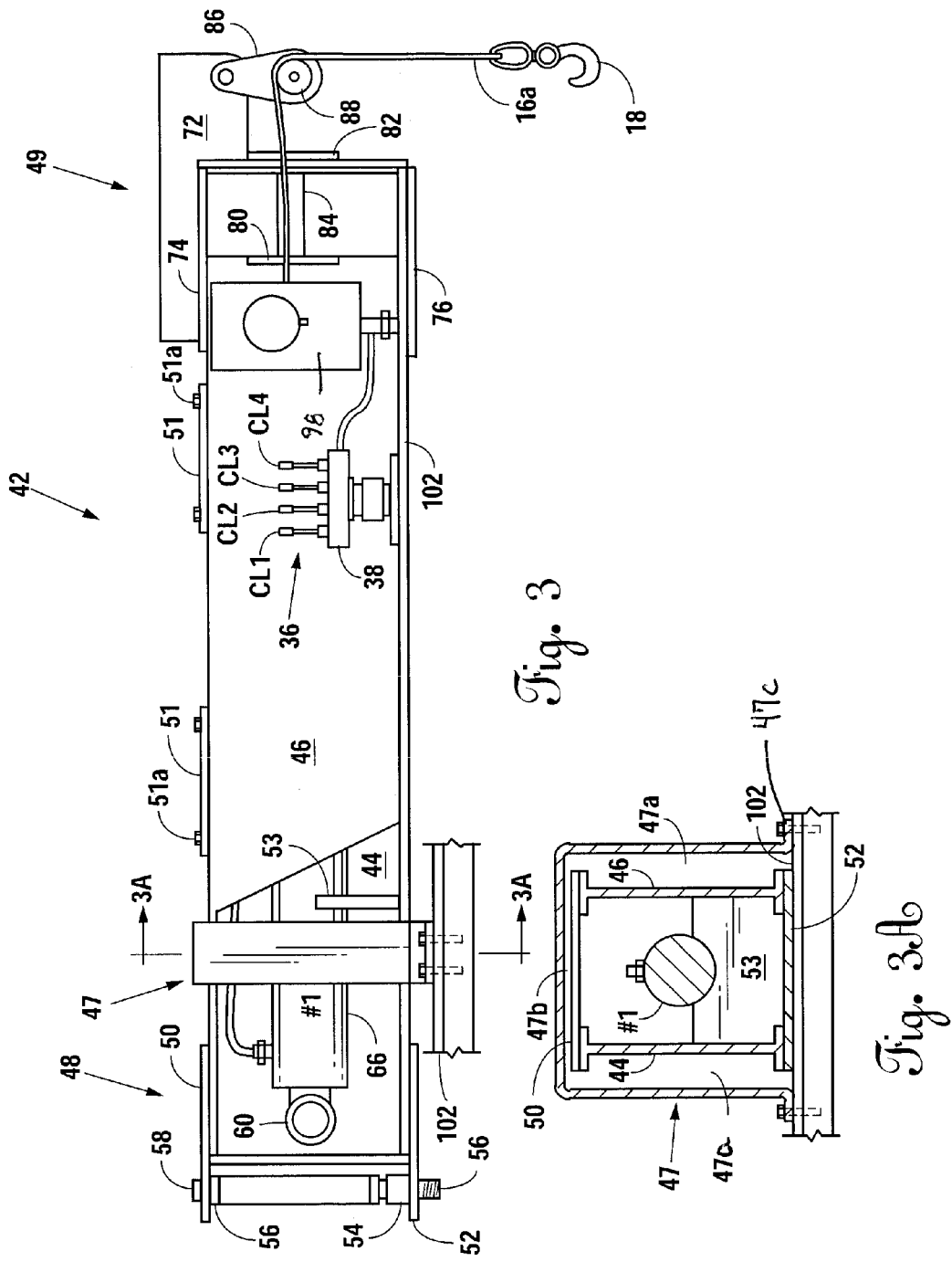
FIG. 3 is a side elevational view of a frame and related elements of a tension application assembly of Applicant's system for testing in-ground anchors.

Turning now to FIG. 2, a hydraulic pressure distribution system 26 is provided, which systems are generally known. Typically such systems include an engine 28 or electric motor E, a pump 30 or P to drive hydraulic fluid, and a tank 32 for receipt and as a source of hydraulic fluid. Hydraulic pressure distribution system 26 will distribute hydraulic pressure through a cylinder control assembly 36 to four hydraulic cylinders Nos. 1, 2, 3, and 4, as more specifically set forth below. Cylinder control assembly 36 may include a valve assembly 38 with a control level for each of the four cylinders, here, control level CL1/CL2/CL3/CL4 (see FIGS. 2 and 3) as well as a pressure gauge G/98 and recording device R/100.

Figure 1B:
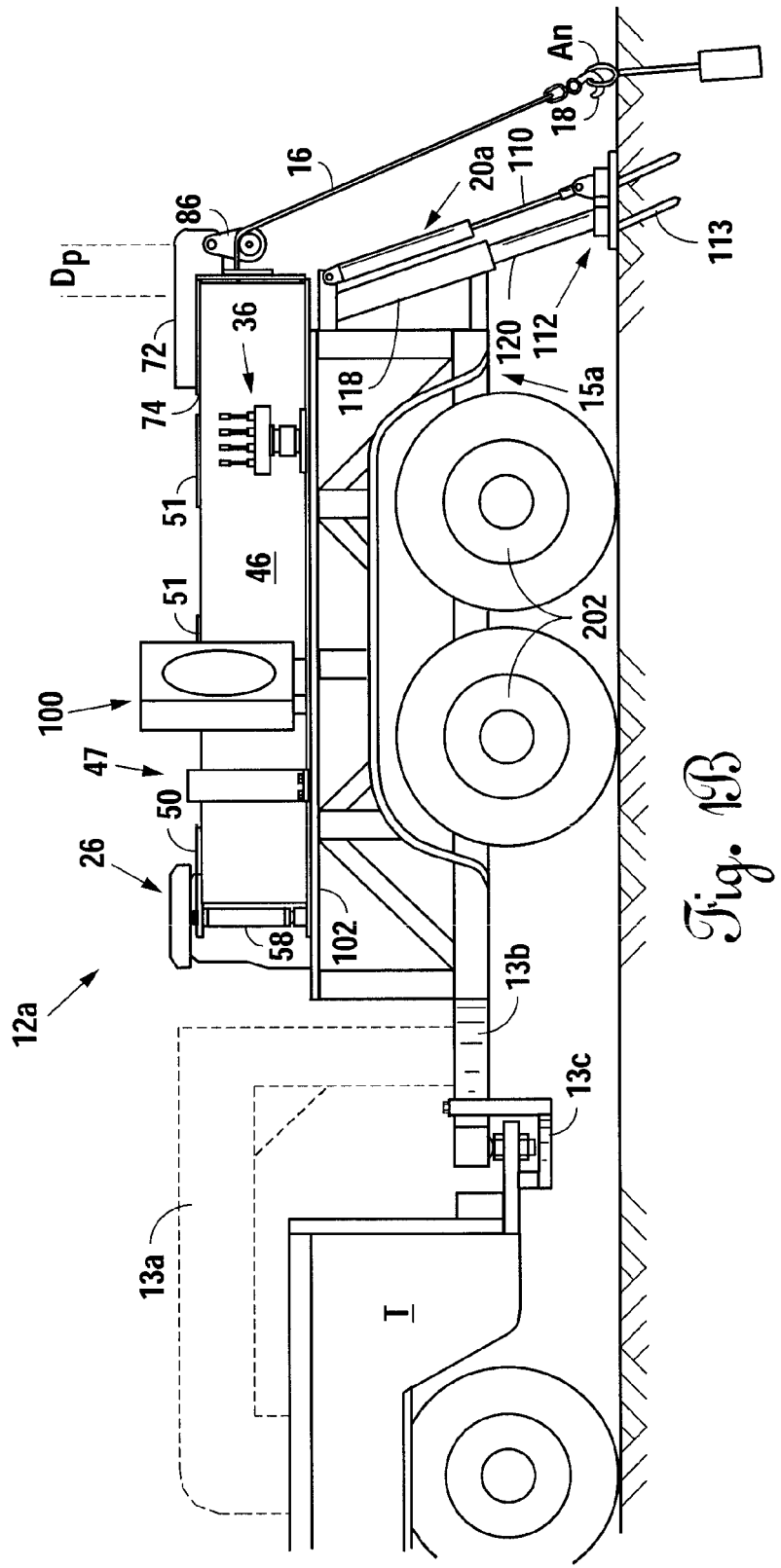
FIG. 1B is a side view of another implementation of Applicant's mobile anchor tester showing use on a trailer, with the trailer hooked up to a tow vehicle, such as a pickup truck.

FIG. 1A illustrates the use of an anti-lift or lift prevention brace 47, which is generally U-shaped (see also FIGS. 1 and 1B). Anti-lift brace 47 has legs 47c with fasteners that will bolt straight down typically into the frame or structure of the truck, trailer or other mobile support system. Moreover, there is a gap 47a between the uprights of the anti-lift brace of about 3 to 4 inches allowing movement of frame 42 to either side under the action of lateral adjusting assembly 90. It has been found in testing that there may be some lifting at the pivot pin or near end of the frame as the hook engaging the anchor attempts to pull the anchor out of the ground by asserting tension. Tension of up to 18,000 lbs. is typically applied and may be held for a period of time, such as 60-120 seconds. If frame 42 tends to lift at near end 48, then the anti-lift brace 47 will catch it and prevent from lifting further, but will also allow the frame, since there is a gap 47a, to move laterally. A gap 47b is also provided at the upper surface of side members, typically about ¼ inch. The anti-lift brace may also be placed closer to the removed end of the frame.

Figure 4:
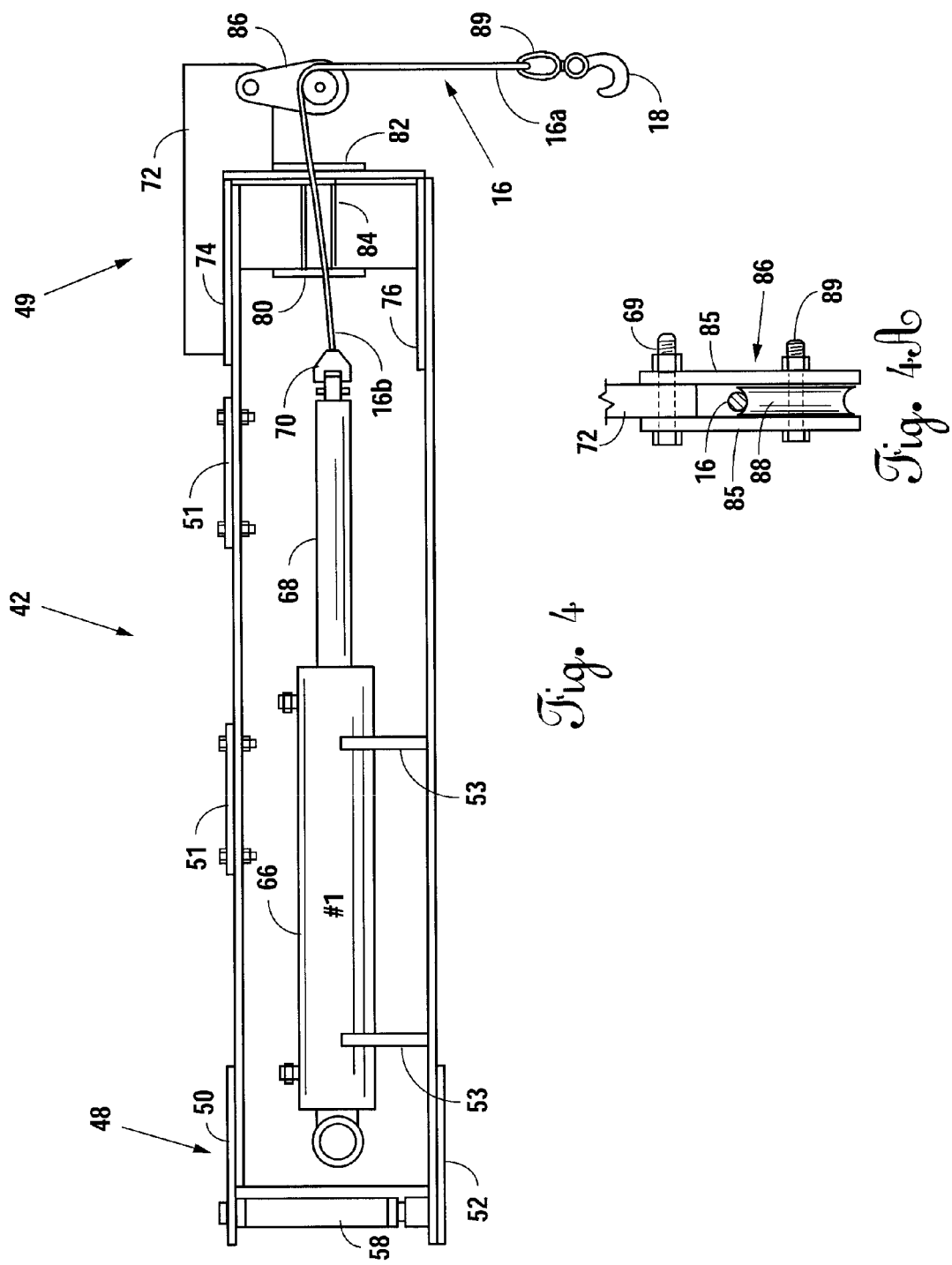
FIG. 4 is a side cutaway view of the tension application assembly, including the frame thereof.
Figure 5:
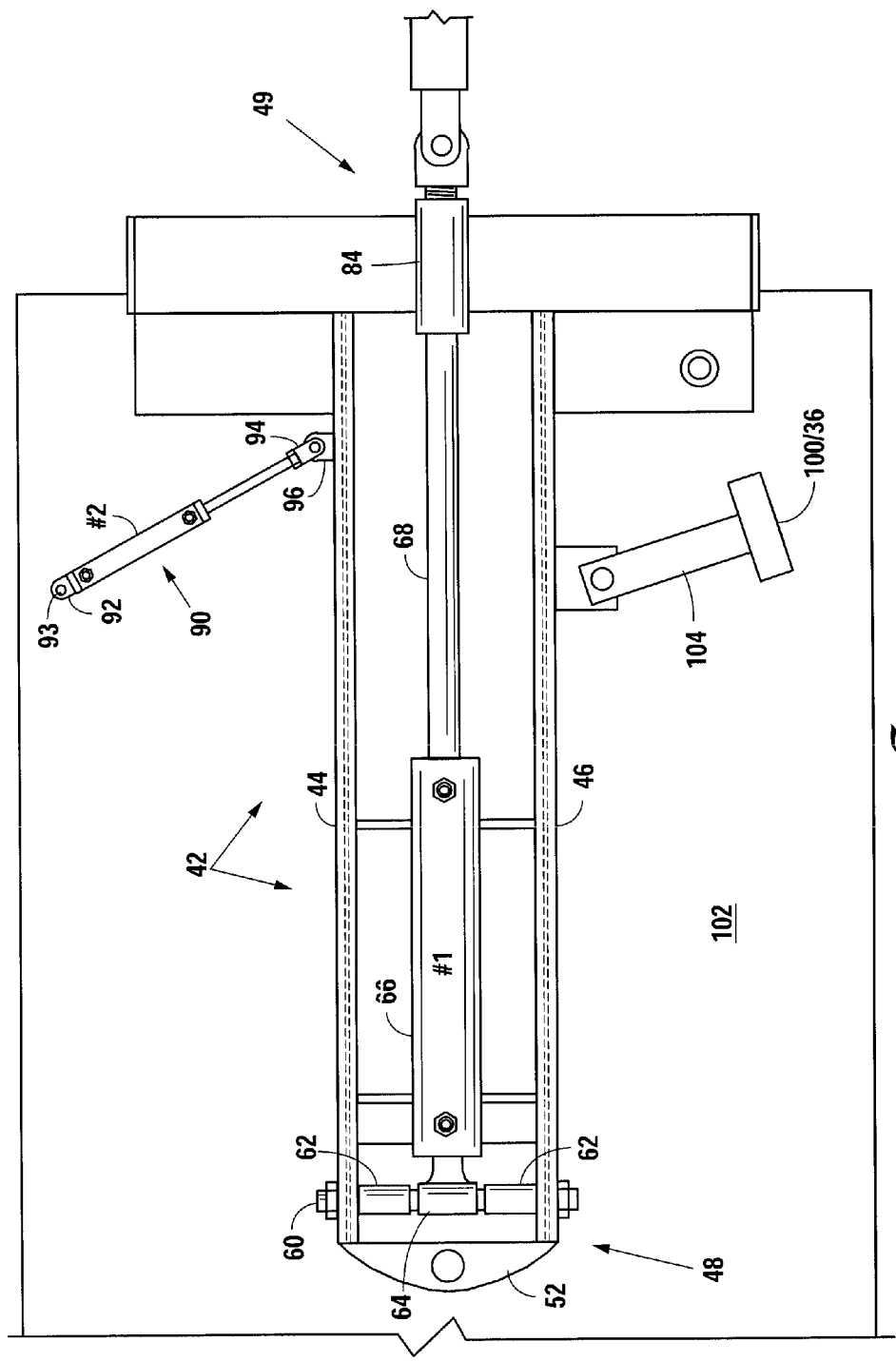
FIG. 5 is a top cross-sectional view of the frame of the tension application assembly.

FIGS. 3 and 4 show the use of steel plate lateral braces 51 that cross from the top surface of the side walls over the top of the cylinder No. 1 to help prevent twisting of frame 42, which lateral braces 51 may be removed/attached with fasteners 51a, which removal allows access to cylinder No. 1. FIGS. 3 and 4, among others, show the use of "U" shaped cradles 53 (e.g., made of steel plate) that cradle the barrel 66. In certain implementations, cradles 53 are welded across from one inner side wall to the other in which the cup shape is open to the top.

As explained above, frame 42 with cylinder No. 1 engaged therewith is designed to pivot about ten inches either way (see FIGS. 6-8) in a slight arc, so as to help position pulley 88 properly. To this end, and because of the great weight of the frame, other elements must be pivoted, lateral adjusting assembly 90 is provided, which typically includes a cylinder No. 2, such as a double acting hydraulic cylinder (see FIG. 5). Cylinder No. 2 is engaged with horizontal support or support plate 102 pivotally through the use of eye 92 mounted to a pin 93, which pin is perpendicular and rigidly mounted. A second eye 94 is engaged at the removed end of cylinder No. 2 and pivotally engages standoff 96, which is coupled (e.g., welded) perpendicular and juts out from side member 44. A control lever CL will allow extension and retraction of the arm of cylinder No. 2 and therefore pivoting of frame 42 about pivot pin 58. It is noted here that the underside of the frame and the related support plates, etc. typically lay flush and are supported on the flat upper surface 102 or any other suitable structural member that will allow the frame to pivot as described while supporting it as it applies tension to an earth anchor. Pivot pin 58 is typically not adapted to support the weight of the frame and other elements thereof.

Cylinder No. 1, which may apply tension to the anchor by retracting arm 68, is controlled through cylinder control assembly, here, control lever CL1, where the Cylinder No. 1 may be retracted or extended by push or pull on the removed end of the lever. A hydraulic pressure distribution system includes lines as known in the art for distributing hydraulic fluid, through the valve assembly 38 to the multiple cylinders of the mobile anchor tester 12. Those lines that are engaged with cylinder No. 1, which is the cylinder that applies tension to cable 16 and to the anchor, typically include a gauge 98 for visually indicating pressure in the cylinder as well as a time/pressure recording graph 100 for indicating change in pressure over period of time. One such recording graph is available from Barton Recorder (0-30,000 pound anchor test recorder). As set forth in FIG. 8, a top view, it is seen that graph 100, cylinder control assembly 36, and/or gauge 98 may be pivotally mounted to frame 42, so as to pivot therewith and make it easier for the operator to have access to the controls and to see the graph after the pulley is properly located. These elements may also be attached to any other suitable structures.

Turning now to FIG. 4A, further elements of the removed end 49 of the frame may be seen. More specifically, it is seen that pulley mounting plate 72 is mounted typically perpendicular to top plate 74 and extends outward therefrom typically to at least the plane of leg assemblies 22/24 and typically about 2 to 12 inches there past. Pulley mounting plate 72 engages a pair of spaced apart pulley bracket plates 85 comprising a pulley bracket 86. Pulley bracket 86 can rotate somewhat on fastener 69 and is adapted to rotatably mount a pulley 88 therebetween on a fastener or other pin 89. Cable 16 is entrained over pulley 88, as seen in FIGS. 4 and 4A.

Further details of adjustable support leg assembly 20 may be seen with respect to FIG. 1A. Both outriggers or assemblies are spaced apart to either side of pulley 88. They include cylinder Nos. 3 and 4, which are rigidly and generally supported (but see FIG. 1B pivot mounting of cylinder near end) to a bumper extension or the mounting platform 106 or other suitable structure of the mobile support platform 12 typically at rear end 15. Both leg assemblies 22/24 are similarly constructed, though independently operated, through control levers CL3 and CL4.

Leg assembly 22 is illustrated in more detail in FIG. 1A. It includes mounted cylinder No. 3 having a barrel 108 and an arm 110. At the removed end of arm 110 is a foot 112. Foot 112, on the upper surface thereof, is engaged to the removed end of arm 110 through a clevis and pivot plate assembly 114 or other rigid foot or pivot foot means. A stabilizer assembly 116 is engaged to the upper surface of foot 112, which typically includes a rigidly mounted sleeve 118, such as 3 inch square steel plate, through which slide 120 is slideably received therein. Stabilizer assembly 116 is mounted so that it is aligned with the longitudinal axis of the mobile support platform 12 and arm 110. Sleeve 118 is rigidly mounted (e.g., by welding or other suitable means) to support member 106. Both assemblies include stabilizers to prevent side loading of arms 110, which could affects seals.

Before testing, independently operated control levers CL3 and CL4 are moved fore and aft, and the two arms 110 will lengthen or contract allowing the user to set feet 112 (two, one for each assembly 22/24) on the ground, and may slightly raise the rear and selectively one side and/or both sides so as to maintain the horizontal support plate 102 or other frame supporting structure in a generally horizontal position when seen viewing the rear of the truck from behind. The pulley should be aligned with the axis of the removed end of arm AN, and the plane of the pulley should be generally perpendicular to the earth's surface and lay in a generally vertical plane, which typically is the plane of the arm coming out of the ground. However, if the arm coming out of the ground is tilted and is non-vertical with respect to the ground, then the selective adjustment of cylinder Nos. 3 and 4 may place the cable in such proper plane.

FIG. 1B illustrates that the adjustable leg support assemblies may be built so that they engage the earth or other support surface at an angle, which generally approximates the angle of the anchor AN in the earth. Further, foot 112 may have one or more toes 113 extending downward therefrom as seen in FIG. 1B.

FIG. 1B illustrates the use of a trailer as Applicant's mobile support platform. When a trailer is used, a truck T may be provided and the truck T may be engaged as by a gooseneck assembly 13a, a bumper hitch assembly 13b, a fifth wheel assembly or any other suitable means to the truck or other suitable vehicle. When a trailer is used as a mobile support platform and when a bumper hitch 13b is used, a safety anti-lift bracket 13c may be provided at the coupling point of the trailer to the ball and bumper hitch of the truck T. This may be an appropriately configured member (e.g., made of steel) that prevents a lifting force at the ball joint end of the trailer from separating the trailer from the truck. Bracket 13c is typically provided only when the truck is stationary. The trailer may stay engaged to the tractor, truck or other pull vehicle during an anchor test or may be removed.

FIGS. 1B and 9-13 illustrate an alternate preferred embodiment of Applicant's device wherein the mobile platform is secured to a trailer rather than a truck. Securement of the trailer to the truck or other tow vehicle may be done by any means known in the art, such as the gooseneck assembly 13a or a bumper hitch assembly 13b as seen in FIG. 1B. As trailer beds are sometimes low, Applicant's device may provide for a support chassis 215 to stand above a trailer frame 200 and axles of a standard trailer.

Trailer frame 200 may include longitudinal members 206 and cross-members 208 or other suitable members, such as welded up steel members. To support the trailer, one or more axles 202 are provided with wheels and tires at the removed ends thereof. If a bumper hitch assembly 13b is used, it typically includes a ball engagement portion 204, for engagement with a ball (not shown) engaged to a frame or bumper mount of a tow vehicle.

Typically, trailer frames 200 have a rear cross-member 210 and a front cross-member 212 which, along with side members (longitudinal members 206) define a generally rectangular base, which engages one or more axles, and on which Applicant's support chassis 215 may be mounted. Support chassis 215 provides a generally horizontal upper surface 215a on which a frame 248, which may be identical, substantially similar or as set forth herein below, is mounted. Frame 248 set forth below has some structural features that are different, but is substantially similar in its functional attributes to the frame 48.

Figure 9:
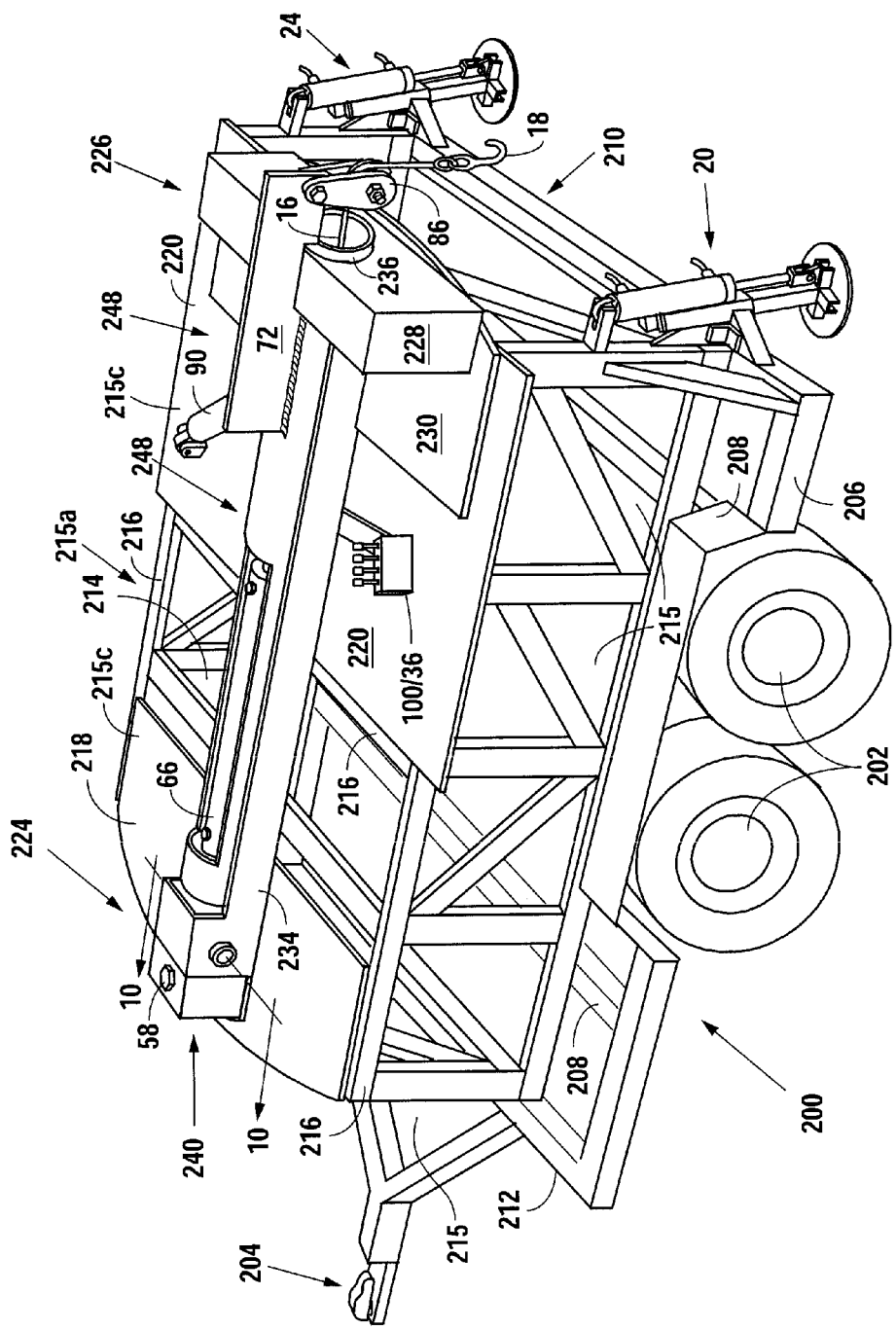
FIG. 9 is a top side perspective view of another example implementation trailer based implementation of Applicant's mobile anchor tester.

Upper surface 215a is a support surface frame 248 above the trailer bed and will typically include a near end plate 218 and a removed end plate 220, which are typically mounted to upper cross-members 216 or other suitable structure. As can be seen in FIGS. 1B and 9, support chassis 215 may include multiple steel braces welded or otherwise engaged to one another to provide a strong rigid horizontal support surface or plate, which is in turn rigidly engaged to trailer frame 200. In turn, axle or axles 202 support the trailer frame, the support chassis, and all other elements of Applicant's device and are attached to a suitable tow vehicle.

Frame 248 is pivotally engaged to upper surface 215a, typically at near end plate 218. Pivotal mounting of anchor testing assembly or engagement unit 214 may be in any suitable arrangement. Frame 248 has a near end 224 and a removed end 226. Near end 224 may be pinned to near end plate 218 (so as to rotate) in any suitable manner, one of which is illustrated below. The underside of frame 248 is supported on upper surface of plates 218/220, but removed end 226 may pivot in an arc through the action of lateral adjusting assembly 90.

Figure 13:
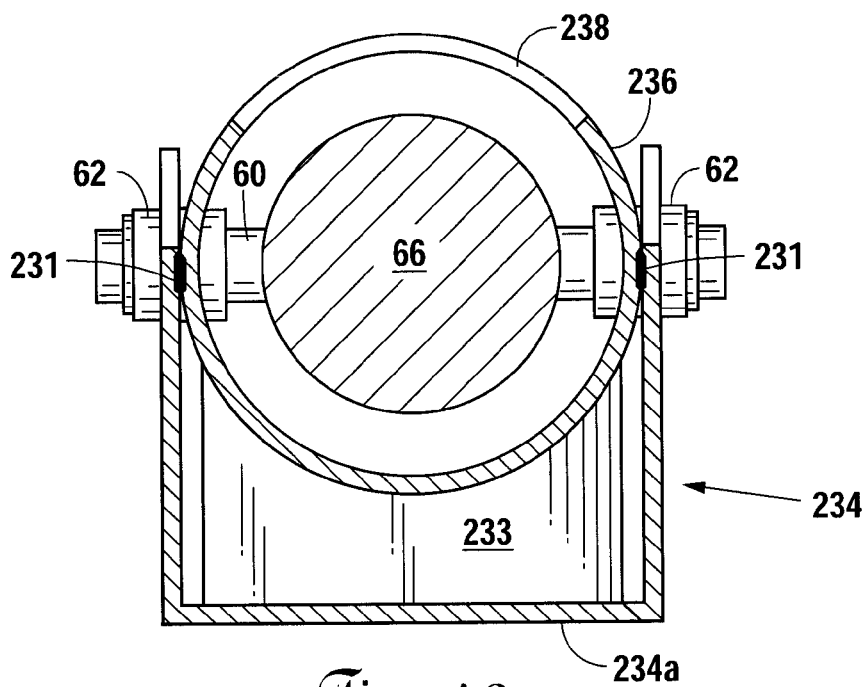
Figure 13A:
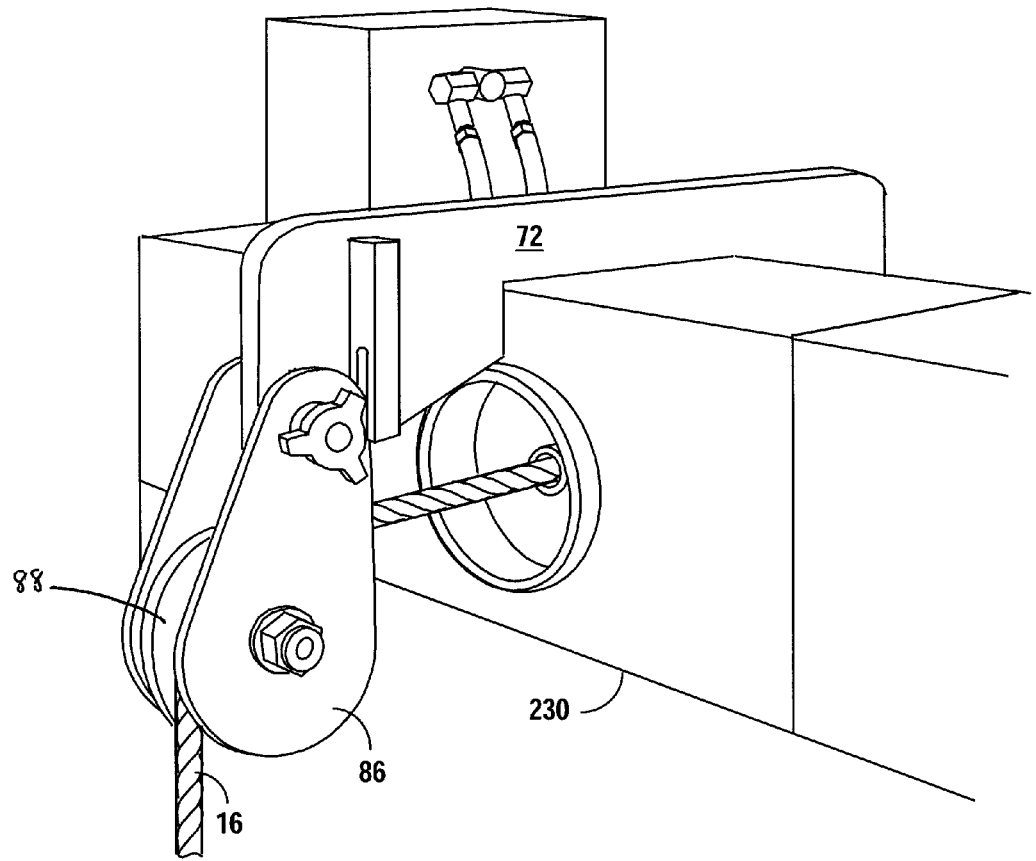
FIG. 13A is a perspective view of a removed end of an embodiment of the anchor engagement unit.
Figure 14:
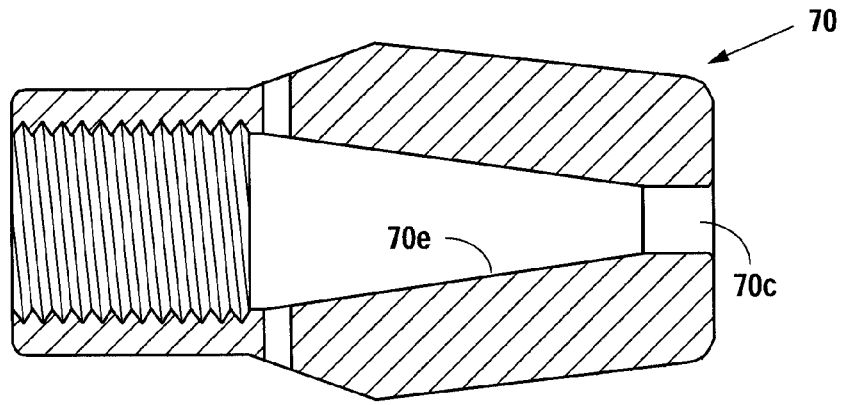
FIGS. 14, 15, and 16 are elevational views of a bullet that engages the cable to the barrel of a cylinder.

Frame 248 serves the same function as frame 48 of the earlier embodiment, but may have different structure to provide additional or enhanced rigidity. In the embodiment illustrated in FIGS. 1B and 9-13, frame 248 includes a U-shaped channel 234, which U-shaped channel includes bottom plate portion 234a and straight side plate portions 234b. This channel member may, for example, be ½ inch thick heavy duty steel plate. Frame 248 may also include a cylindrical steel pipe 236, whose outer diameter is about the distance across between the two side plates 234b as best seen in FIG. 13. This tube may, for example, be ½ inch wall, 7 inch O.D. heavy duty steel pipe. Both U-shaped channel 234 and pipe 236 lay so that their longitudinal axes are aligned, and pipe 236 may be welded to side plates near the upper portions thereof as seen at welds 231 in FIG. 13. One or more vertical support plates 233 may also assist in locating the pipe and the U-shaped channel with respect to one another and rigidly maintaining the structural integrity of the unit while tension, sometimes up to 20,000 lbs., is generated when the anchor is tested.

The previous embodiment has some different structural features, including a pair of I-beams acting as side members. In the embodiment illustrated herein, a U-shaped channel element and a cylindrical element mounted one to the other provide rigidity.

Lateral adjusting assembly 90 is typically pivotally pinned at a removed end thereof to upper surface 215a of the support chassis, and a near end is attached to one of the side walls of the U-shaped channel. Likewise, graph and cylinder control assembly 100/36 may be mounted to a standoff from one of the side walls, so as to pivot therewith in the same manner as the earlier embodiment illustrating frame 248 described hereinabove.

Near end 224 of frame 248 may include a boxed pin and axle support assembly 240 as seen in FIGS. 1B and 9. Steel plates and/or steel members may "box" the near end of the U-shaped channel in a steel box-shape structure for articulating on a pivot pin 58. Any strong suitable structure, which may, for example, include welded up steel plates and/or steel members, may be used. The under side of boxed assembly 240 may be supported on an upper surface of near end plate 218, so it pivots.

Removed end 226 of anchor engagement unit 214 may include a steel plate base 230, which may be rigidly welded with the removed end of U-shaped channel 234, so as to move therewith. On base 230, a pulley support assembly 228 may be provided, which may include tube 236, pulley 88, and bracket assembly 86. Bracket assembly 86 is rigidly engaged to the removed end of tube 236 to trending longitudinally through pulley and support assembly 228. Pulley support assembly 228 may be built up from steel plate or other suitable material and will provide rigidity for the pulley and pulley bracket to resist the large forces generated when the anchor is tested. Thus, side walls and bottom walls are typically rigidly engaged to pulley support assembly 228 and base 230 as well as the removed end of tube 236, and is aligned to centrally locate cable 16 and pulley 88 in alignment with the arm 68 of barrel 66. A bullet 70 may be provided for engaging the near end of the cable to the removed end of the hydraulic arm. Bushings 62, collar 64, pivot pin 58, and axle 60 may be provided substantially, structurally, and functionally as set forth in the previous embodiment.

Turning to FIGS. 4, 14, 15, and 16, it is seen that near end 16b of cable 16 may be engaged to a bullet 70 and pinned to the removed end arm 68. Bullet 70 may be filled with babbitt to help secure bullet 70 to cable end 16b.

Figure 15:
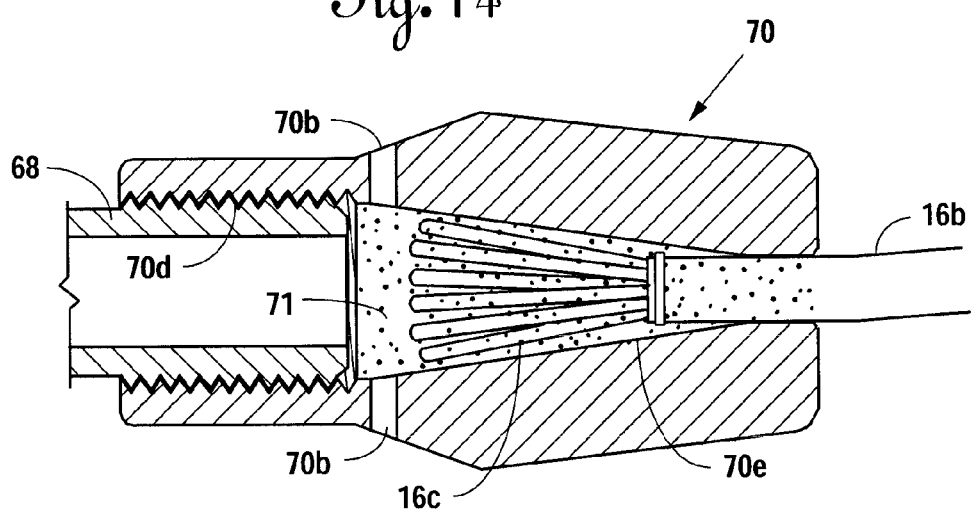
Figure 16:
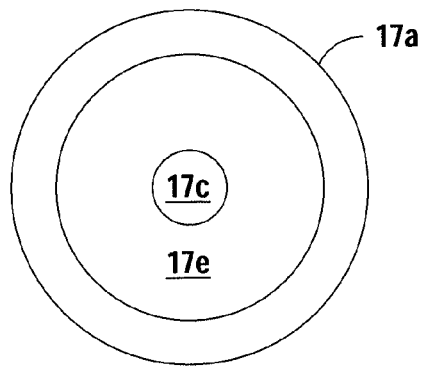

FIGS. 4, 14, 15, and 16 illustrate views of the bullet 70. Bullet 70 is provided to firmly engage near end 16b of cable 16 to the removed end 68 of the arm of cylinder #1. This must be an especially strong junction because of the significant tension when arm 68 is retracted. Bullet 70 includes a machined steel socket 70a having a cable opening 70c on one end thereof, threaded section 70d on the other end thereof, and one or more weep holes 70b near where the threaded portion 70d meets conical inner walls 70e. Removed end 16b includes a frayed portion 16c, wherein the individual strands of the multi-strand cable are unraveled and spread out as illustrated in FIG. 15. Removed ends of hooked, cable strands 16c are located substantially within the conical walls and the inner volume of the socket 70a, that is past the threaded portion 70d as best seen in FIG. 15. Babbitt metal 71 substantially encases removed end 16b of cable 16 to the extent that the removed end is within the socket 70a.

All dimensions herein are typical and approximate and may be varied as is suitable to a particular application. In preparing the bullet 70, the unfrayed cable is entrained in socket 70a by threading it through cable opening 70c. Cable opening 70c is typically about 0.7 of an inch in diameter, and cable may be ⅝ inch 20,000 lb. test cable or any other suitable cable. After threading the end through cable opening 70c and beyond the threaded portion 70d, the exposed end of the cable may be spread out and hooked. When spread strands 16c are sufficiently spread, then the unfrayed portion is pulled back so the spreaded strands are substantially within the conical inner walls as seen in FIG. 15.

With the bullet 70 in a vise and held vertical and a rag wrapped around the area where the cable enters cable opening 70c, hot Babbitt metal 71 may be poured vertically into the interior until it comes out of the weep hole. This will spread the Babbitt material, before it solidifies, in and among and in close proximity to and adjacent with hooked cable strands 16c. When the Babbitt metal solidifies and cools, the assembly is then removed from the vise and, if necessary, the removed end of the arm 68 is tapped with threads to match the threaded portion 70d of socket 70a. The threaded portions are then joined by threading and by secure fit of the cable to the arm is achieved.

Figure 17:
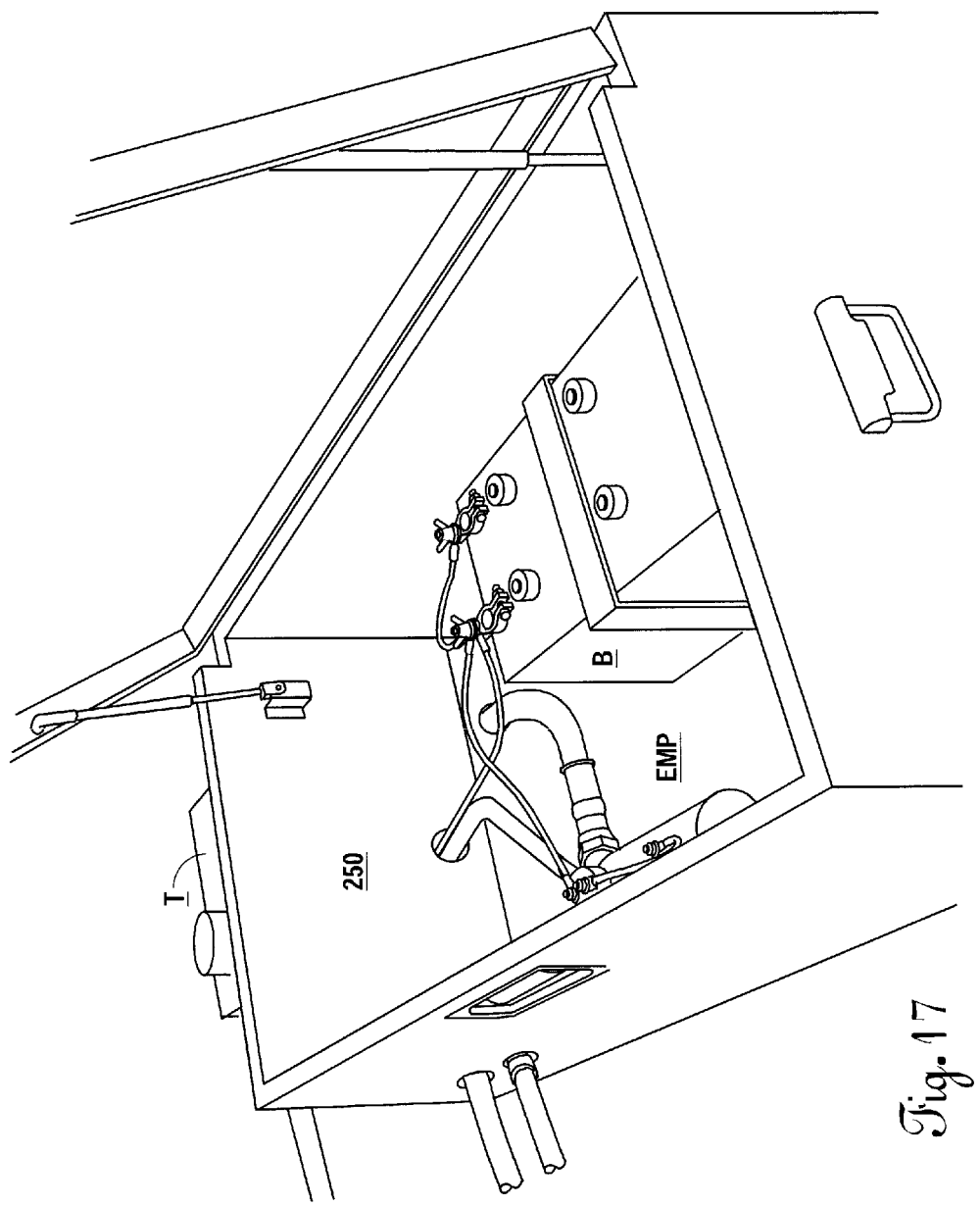
FIGS. 17 and 18 are perspective views of an electric motor pump and battery used to energize and provide fluid pressure in Applicant's hydraulic pressure distribution system.
Figure 18:
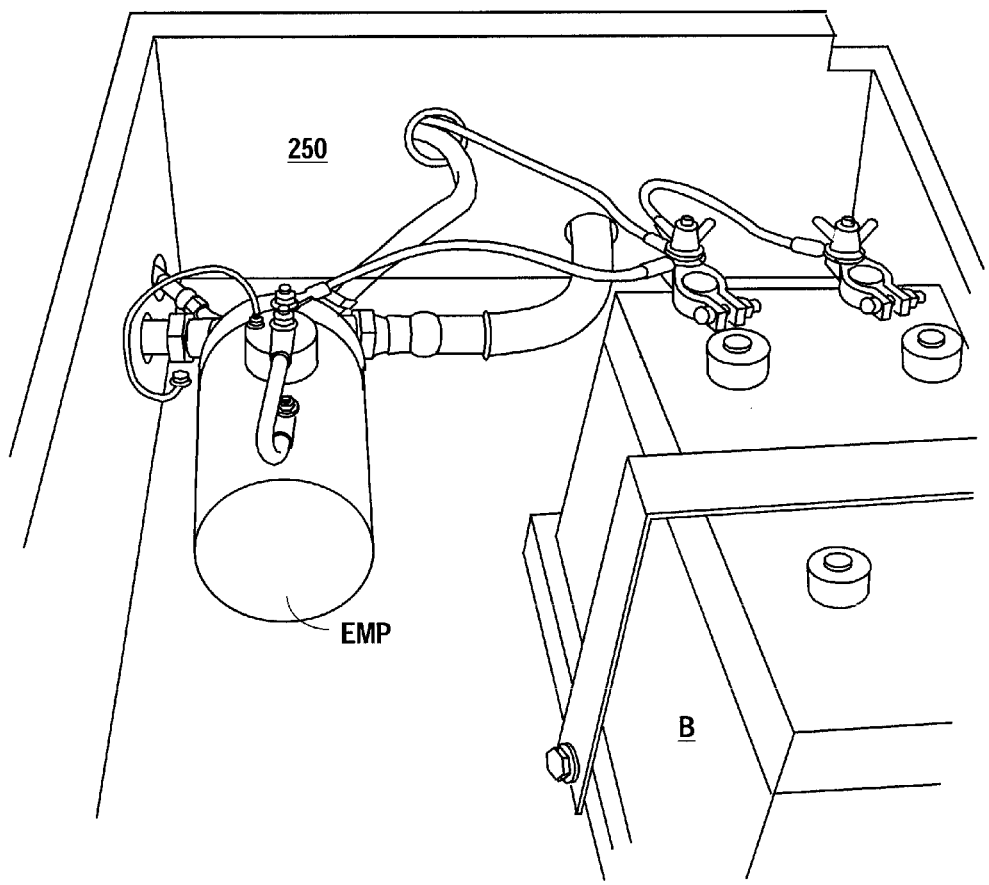
Figure 19:
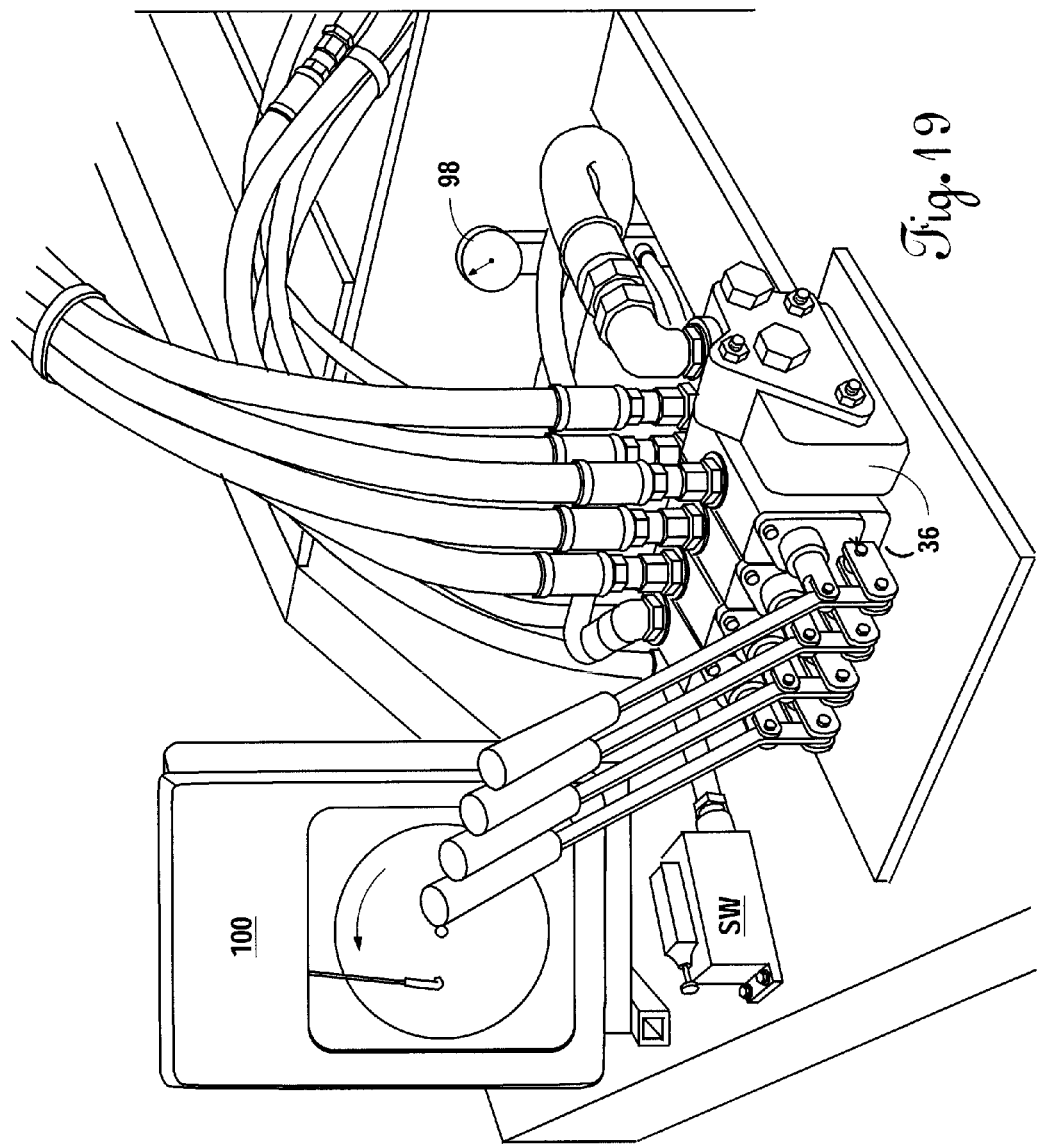
FIG. 19 illustrates a close-up view of the cylinder control assembly and related elements thereof in perspective view.

FIGS. 17 and 18 illustrate an electric motor and fluid pump unit EMP, such as known in the art of hydraulic fluid control systems, which may be energized through a battery B. EMP and battery B may be enclosed within a steel box 250, which may be mounted in any suitable location, including the near end 224 of the horizontal surface or other structure. EMP may be controlled through an operator control switch SW (see FIG. 19), which lays adjacent cylinder control assembly 36, and indeed may be mounted in one embodiment to move therewith.

In a preferred embodiment, an electric motor is provided for the hydraulic pump. One electric motor is an SPX Stone 12 v DC motor with a pump designed to pump about 15 gallons per minute of hydraulic fluid at up to 2500 psi (although one would typically not need to go that high to reach the 18,000 pound pull limit on the anchor). In another embodiment, a 14 hp Honda was tested with a DC 30 pump, again up to 2500 psi and set to pump hydraulic fluid at 15 gallons per minute.

The four-way valve cylinder control assembly 36 with multiple levels may be available from Prince and is rated up to 2500 psi. A release valve may be set on the four-way valve to release at 18,000 pounds.

The two leg assemblies 22/24 may use either a Redline ram 2×5 inch bore or Hercules 2½×5 inch ram. Both of these are double acting. The sliding leg extensions are provided to prevent any side loadings on the cylinders. The angle of the outriggers or leg assembles is, in a preferred embodiment, slanted backward to proximate the angle between the removed end of the anchor (where the cable hook attaches to the anchor arm) and the center of the pulley as best seen in FIG. 1B. In other words, the cable angle between the pulley and the anchor is about the angle that the leg assemblies take with the ground (therefore, preventing a moment arm developing that might tip the trailer or truck). A range of angles for the leg assemblies is about 0°-45°, preferred about 5°-30°. ⅝ inch multi-strand wire rope available from Caldwell Rope Co., Oklahoma City, Ok., may be used for the cable. The hook is available from Dunnevo and is rated at 32,000 pounds. The pulley may be a 6" McKissick pulley rated at 12 tons, Model No. N402.

Typically, the operator of the truck or truck with trailer will use the camera system (on truck or trailer) to back up to the earth anchor so the arm extending therefrom will, along an imaginary extended axis, go through the center of the pulley. The operator may then use cylinder No. 4 to move the frame side to side to make sure there is no side loading placed on the cylinder or arm of cylinder No. 1 during the testing phase.

In one embodiment, the pulley is about 3 feet off the ground and the exposure of the arm above the ground is several inches up to about a foot. This leaves about two feet between the center of the pulley and where the hook engages the arm from the anchor.

Although the invention has been described in connection with several embodiments, it is not intended to limit the invention's particular form set forth, but on the contrary, it is intended to cover such alterations, modifications, and equivalences that may be included in the spirit and scope of the invention as defined by the appended claims.

The invention claimed is:

1. A device for testing the tension bearing capabilities of in-ground anchors or the like, the device comprising:
   a wheeled, mobile platform having a generally horizontal support surface, the horizontal support surface having a removed edge, the horizontal support surface spaced above the ground, the wheeled, mobile platform having a front end, and a rear end;
   an anchor testing assembly engaging the horizontal support surface, having a cable at a removed end adapted to engage the in-ground anchor and applying tension thereto;
   a first adjustable leg assembly having a body and a leg, the body rigidly engaged with the mobile platform and spaced apart from the ground with the leg extendable and retractable therefrom, the removed end of the leg capable of reaching the ground when in an extended position and off the ground in a retracted position; and
   a second adjustable leg assembly having a body and a leg, the body rigidly engaged with the mobile platform and spaced apart from the ground with the leg extendable and retractable therefrom, the removed end of the leg capable of reaching the ground when in an extended position and off the ground in a retracted position.

2. The device of claim 1, wherein the mobile platform either is a truck or a trailer.

3. The device of claim 1, wherein the anchor testing assembly includes a first hydraulic cylinder adapted to apply tension to the cable; and wherein the first and second adjustable leg assemblies comprise second and third hydraulic cylinders; and further including means to selectively apply hydraulic force to the hydraulic cylinders, said means including an electric motor and pump.

4. The device of claim 3, further including means to display a hydraulic force to one or more of the hydraulic cylinders.

5. The device of claim 4, wherein the means to display hydraulic forces includes means to record the magnitude of the application of pressure to the first double acting cylinder as a function of time.

6. The device of claim 3, wherein the anchor testing assembly includes a frame configured to lay adjacent and on top of the horizontal support surface of the mobile platform, the frame pivotally attached at a near end thereof to the horizontal support surface of the mobile platform, the frame adapted to secure the first cylinder thereto, wherein the first cylinder comprises a barrel and a rod, and wherein the cable is attached to the removed end of the rod.

7. The device of claim 6, wherein the frame further includes a pulley at the removed end thereof, the pulley for entraining the cable thereon.

8. The device of claim 7, further including a bullet for attaching the first hydraulic cylinder to the cable.

9. The device of claim 7, wherein the pulley extends beyond the removed edge of the horizontal support surface.

10. The device of claim 6, wherein the frame includes top, side, and bottom walls configured to at least partly enclose the first cylinder and boxed sections at a near and removed end thereof.

11. The device of claim 7, wherein the frame is engaged with a fourth hydraulic cylinder, the fourth hydraulic cylinder for further engaging the horizontal support surface and the frame such that the removed end of the frame moves in an arc, the arc in a plane generally parallel to the horizontal support surface.

12. The device of claim 1, wherein the mobile platform is a dual axle trailer.

13. The device of claim 1, further including a bracket for engaging the horizontal support surface and the frame to prevent the frame from substantially lifting off the horizontal support surface.

14. The device of claim 1, wherein the wheeled, mobile platform includes a video system adapted to guide a driver thereof in positioning the wheeled, mobile platform proximate the in-ground anchor.

15. The device of claim 1, wherein first and second adjustable leg assemblies lay adjacent and spaced apart from the cable at the removed end of the anchor testing assembly.

16. The device of claim 1, wherein the adjustable leg assemblies make an angle of between about 5 degrees and about 30 degrees outward from vertical.

17. A device for testing the tension bearing capabilities of in-ground anchors or the like, the device comprising:
   a wheeled, mobile platform having a generally horizontal support surface having a removed edge spaced above the ground, the wheeled, mobile platform having a front end, and a rear end;
   an anchor testing assembly engaging the horizontal support surface, having a cable at a removed end adapted to engage the in-ground anchor and applying tension thereto;
   a first adjustable leg assembly having a body and a leg, the body rigidly engaged with the mobile platform with the leg extendable and retractable therefrom, the removed end of the leg capable of reaching the ground when in an extended position;
   a second adjustable leg assembly having a body and a leg, the body rigidly engaged with the mobile platform with the leg extendable and retractable therefrom, the removed end of the leg capable of reaching the ground when in an extended position;
   wherein the mobile platform either is a truck or a trailer;
   wherein the anchor testing assembly includes a first hydraulic cylinder adapted to apply tension to the cable; and wherein the first and second adjustable leassemblies comprise second and third hydraulic cylinders; and further including means to selectively apply hydraulic force to the hydraulic cylinders;
   wherein the anchor testing assembly includes a frame configured to lay adjacent and on top of the horizontal support surface of the mobile platform, the frame pivotally attached at a near end thereof to the horizontal support surface of the mobile platform, the frame adapted to secure the first cylinder thereto, wherein the first cylinder comprises a barrel and a rod, and wherein the cable is attached to the removed end of the rod;
   wherein the frame further includes a pulley for engaging the removed end thereof, the pulley for entraining thereon, the cable;
   wherein the frame is engaged with a fourth hydraulic cylinder, the fourth hydraulic cylinder for further engaging the horizontal support surface and the frame such that the removed end of the frame moves in an arc, the arc in a plane generally parallel to the horizontal support surface; and
   wherein all the hydraulic cylinders are double-acting hydraulic cylinders.

18. The device of claim 17, wherein the means to selectively apply hydraulic force includes a hydraulic cylinder pressure distribution and control system, including multiple cylinder control levers and an electric motor and pump to drive a hydraulic fluid through the pressure distribution and control system to the cylinders.

19. The device of claim 18, further including means to display a hydraulic force to one or more of the hydraulic cylinders.

20. The device of claim 19, further including a switch for controlling the electric motor, the switch proximate the means to display and the control levers such that the operator may watch the display while operating the switch and the cylinder control levers.

21. A method of using the device of claim 17 on a ground anchor having an embedded portion and longitudinal member attached to the embedded portion and extending outward from the ground, the longitudinal member having a removed end, the method comprising the steps of:
   positioning the mobile platform such that the pulley is aligned with an imaginary axis extending beyond the removed end of the longitudinal axis;
   attaching the removed end of the cable to the removed end of the longitudinal member; and
   applying hydraulic pressure to the first hydraulic cylinder so a to create tension in the longitudinal member.

* * * * *